United States Patent [19]

Scheetz

[11] 4,277,389
[45] Jul. 7, 1981

[54] X RAY SCATTERING DEVICE

[75] Inventor: Howard A. Scheetz, Lancaster, Pa.

[73] Assignee: The Polymer Corporation, Reading, Pa.

[21] Appl. No.: 90,884

[22] Filed: Nov. 5, 1979

[51] Int. Cl.³ .......................................... C08L 77/00
[52] U.S. Cl. ................................................ 260/37 N
[58] Field of Search ............... 260/37 N, 42.27, 42.46; 252/63.5

[56]  References Cited

U.S. PATENT DOCUMENTS

| | | | |
|---|---|---|---|
| 2,969,327 | 1/1961 | Quehl | 252/63.5 |
| 3,546,017 | 12/1970 | Pendleton et al. | 427/32 |
| 3,698,393 | 10/1972 | Stone | 128/296 |
| 3,911,922 | 10/1975 | Kliger | 128/296 |
| 4,118,532 | 10/1978 | Homsy | 260/42.27 |

FOREIGN PATENT DOCUMENTS 851775   9/1970   Canada.

OTHER PUBLICATIONS

Chemical Abstracts; Study on Barium Titanate by a Semiconductor Detector; Shimei; vol. 85, 115025j.

*Primary Examiner*—Lewis T. Jacobs
*Attorney, Agent, or Firm*—Richard O. Church

[57]     ABSTRACT

An X ray scattering device for implantation in the human body is disclosed which is comprised of finely divided barium titanate uniformly dispersed in a non-toxic plastic binder.

4 Claims, No Drawings

X RAY SCATTERING DEVICE

BACKGROUND OF THE INVENTION

In certain surgical procedures various articles are implanted in the human body for a limited period of time. For example, when malignant growths are surgically removed from the body, it is sometimes desirable to implant small vials containing radioactive substances in the region where the malignancy was removed. This provides a localized low level of radiation which can be effective to destroy any remaining traces of malignancy in tissue which was not removed. After the radioactive implant has been in the patient for an effective period of time, the implant is surgically removed.

One complication that has arisen in the use of these radioactive implants is that, after the original incision has healed and possibly a small migration of the implant has occurred, the surgeon may find it difficult to locate the precise position of the implant without probing and causing unnecessary distress to the patient. To overcome this problem, it has been proposed to include a small object that will produce an image on an X ray screen or photographic film that will accurately locate the implant prior to surgical removal. The selection and design of such a device is subject to several complicating factors.

First, any substance that is implanted in the human body must be nontoxic and, for this reason, some of the more common materials that are known for their ability to absorb X rays, such as lead, cannot be considered. Second, the device should be made as small as possible to avoid unnecessary discomfort to the patient and this dictates that the locator device be made from materials that will be effective in only small amounts to leave an image on an X ray screen.

Accordingly, it is an object of this invention to provide an article for implantation in the human body which is nontoxic and which will leave a distinct image on an X ray screen or photographic film.

These and other objects of this invention are achieved by incorporating finely divided barium titanate in a film forming polymeric matrix. It has been found that small chips or wafers of such a material when implanted in an animal body, are effective to scatter X rays and leave an image on an X ray screen or film. Suitable polymers for use as a matrix material that are nontoxic and have good chemical resistance to body fluids include, for example, polyamides, polyolefins and fluorocarbons such as polytetrafluoroethylene.

To obtain good scattering of X rays in thin sections, e.g. from about 2 to 100 mils, it is important to work as much barium titanate into the polymeric matrix as it will accept as is consistent with maintaining good enough physical properties to enable handling and shape formation. This requires obtaining a thorough dispersing of barium titanate in the polymer. For example, with proper care, upwards of 50%, and as much as 60% by weight barium titanate can be worked into a nylon matrix. A thorough dispersion of the barium titanate throughout the nylon is also important in order to obtain reproducable and uniform X ray scattering.

To achieve the desired degree of dispersion, it is convenient to melt-mix the polymer and the barium titanate under conditions of intensive mixing such as may be generated in a twin screw compounding extruder. The melt-mixed material may then be extruded directly into a strip or sheet from which a convenient shape may be stamped. Alternatively, small diameter rods may be extruded, chopped and pelletized for subsequent extrusion into a desired shape at a more convenient time.

As the high filler loading of barium titanate is abrasive and dulls cutting tools, it has been found most convenient to extrude sheets of material in the desired thickness, to slit the sheets into strips, and stamp small diameter buttons from the strips. Buttons about ½ inch in diameter and about 1/16 of an inch thick have proven to be particularly useful. They are not so large as will cause distress to the patient, but are large enough to leave a clearly defined image on an X ray screen or film when implanted in animal tissue.

EXAMPLE

Finely divided nylon (less than 1 micron) was prepared by dissolving nylon in hot glycol and precipitating the fine powder from solution. The process used in the preparation of the finely divided nylon is described in detail in U.S. Pat. No. 2,639,278.

Sixty parts by weight of a commercially available barium titanate having a particle size of about 44 microns, was mixed with 40 parts by weight of the precipitated nylon in elbow type mixer having an internal paddle. The mixing was completed in about two minutes. Note that the mixing time should be kept at a minimum amount so that the nylon and barium titanate will not separate due to the considerable difference in their densities.

After the mixing was complete, the mixture was extruded through a Leistritz twin screw compounding extruder and the product was pelletized to form a molding powder suitable for feeding to an extruder.

At a later time, the molding powder was extruded into a 1/16 inch thick sheet which was slit into ¾ inch strips from which ½ inch round buttons were stamped. The buttons, when implanted in the human body, proved effective in scattering X rays so as to be clearly observable as opaque spots on an X ray film.

While it is convenient to use precipitated nylon, ground nylons are equally effective in the practice of this invention. It is preferred, however, in order to obtain good mixing, that the nylon particles be at least as small as the barium titanate particles. Other useful polymeric materials are dispersion grades of polytetrafluoroethylene and finely divided polyethylene and polypropylene which are available in the marketplace.

I claim:

1. A method for the preparation of an X-ray scattering device comprising the steps of intimately blending at least 50 weight percent of finely divided barium titanate having a particle size less than about 44 microns with submicron nylon particles prepared by a dissolution and precipitation process and melting the mixture under intensive mixing to wet out and disperse the barium titanate particles in the molten nylon, and forming a shaped article.

2. A method according to claim 1 in which the melt-mixed material is extruded in the form of a film of from about 2 to 100 mils in thickness.

3. A method according to claim 1 in which shapes suitable for implantation into a living body are formed from the extruded film.

4. An X ray scattering device adapted for implantation into a living animal tissue comprising at least 50 weight percent of −44 micron barium titanate powder uniformly dispersed in a nylon matrix.

* * * * *